US006642207B1

(12) United States Patent
Horsburgh et al.

(10) Patent No.: US 6,642,207 B1
(45) Date of Patent: Nov. 4, 2003

(54) ARTIFICIAL CHROMOSOME CONSTRUCTS CONTAINING FOREIGN NUCLEIC ACID SEQUENCES

(75) Inventors: Brian Horsburgh, Vancouver (CA); Dong Qiang, Vancouver (CA); Francis Tufaro, Vancouver (CA); Jeffery Ostrove, West Vancouver (CA)

(73) Assignee: MediGene, Inc., San Diego, CA (US)

( * ) Notice: Subject to any disclaimer, the term of this patent is extended or adjusted under 35 U.S.C. 154(b) by 65 days.

(21) Appl. No.: 09/922,271

(22) Filed: Aug. 3, 2001

Related U.S. Application Data (63) Continuation of application No. 09/031,006, filed on Feb. 26, 1998, now Pat. No. 6,277,621.

(51) Int. Cl.[7] ...................... A61K 31/711; C12N 15/86; C12N 15/63; C07H 21/04
(52) U.S. Cl. ...................... 514/44; 435/320.1; 435/69.1; 435/91.1; 435/91.4; 435/455; 435/456; 435/458; 435/325; 435/235.1; 424/93.1; 424/93.2; 424/93.6; 536/23.1; 536/23.72; 536/24.1
(58) Field of Search .............................. 435/320.1, 69.1, 435/91.1, 91.4, 455, 456, 458, 325, 235.1; 424/93.1, 93.2, 93.6; 536/23.1, 23.72, 24.1

(56) References Cited

U.S. PATENT DOCUMENTS

| 5,288,641 A | 2/1994 | Roizman |
| 5,501,979 A | 3/1996 | Geller et al. |
| 5,585,096 A | 12/1996 | Martuza et al. |
| 5,658,724 A | 8/1997 | DeLuca |
| 5,776,745 A | 7/1998 | Ketner et al. |

FOREIGN PATENT DOCUMENTS

| EP | 0 453 242 A1 | 10/1991 |
| WO | WO 90/09441 | 8/1990 |
| WO | WO 95/03400 | 2/1995 |
| WO | WO 96/04394 | 2/1996 |
| WO | WO 96/26267 | 8/1996 |
| WO | WO 97/05263 | 2/1997 |
| WO | WO 97/30732 | 8/1997 |

OTHER PUBLICATIONS

Ascenzioni et al., "Mammalian Artificial Chromosomes—Vectors for Somatic Gene Therapy," Cancer Letters 118:135–142 (1997).

Bilbao et al., "Adenoviral/retroviral Vector Chimeras: a Novel Strategy to Achieve High–efficiency Stable Transduction in Vivo," The FASEB Journal 11:624–634 (1997).

Burke, "Special Section: Yeast Artificial Chromosome Cloning; YAC cloning: options and problems," GATA, 7:94–99 (1990).

Chiou et al., "Mutations in the Herpes Simplex Virus Major DNA–Binding Protein Gene Leading to Altered Sensitivity to DNA Polymerase Inhibitors," Virology, 145:213–226 (1985).

Horsburgh et al., "Allele Replacement: an Application That Permits Rapid Manipulation of Herpes Simplex Virus Type 1 Genomes," Gene Therapy 6:922–930 (1999).

Ketner et al., "Efficient Manipulation of the Human Adenovirus Genome as an Infectious Yeast Artificial Chromosome Clone," Proc. Natl. Acad. Sci. U.S.A., 91:6186–6190 (1994).

Messerle et al., "Cloning and mutagenesis of a Herpesvirus Genome as an Infectious Bacterial Artificial Chromosome," Proc. Natl. Acad. Sci. U.S.A., 94:14759–14763 (1997).

Monaco et al., "YACs, BACs PACs, and MACs: Artificial Chromosomes as Research Tools," TIBTECH 12:280–286 (1994).

Saeki et al., "Herpes Simplex Virus Type 1 DNA Amplified as Bacterial Artificial Chromosome in *Eschericia coli*: Rescue of Replication–Competent Virus Progeny and Packaging of Amplicon Vectors," Human Gene Therapy, 9:2787–2794 (1998).

Shizuya et al., "Cloning and Stable Maintenance of 300–kilobase–pair Fragments of Human DNA in *Escherichia coli* using an F–factor base Vector," Proc.Natl. Acad. Sci. U.S.A., 89:8794–8797 (1992).

Wang et al., "Complete Nucleotide Sequence of Two Generations of a Bacterial Artificial Chromosome Cloning Vector," BioTechniques, 23:992–994 (1997).

Yang et al., "Homologous Recombination Based Modification in *Esherichia Coli* and Germline Transmission in Transgenic Mice of a Bacterial Artificial Chromosome," Nature Biotechnology, 15:859–865 (1997).

*Primary Examiner*—David Guzo
(74) *Attorney, Agent, or Firm*—Clark & Elbing LLP (57) ABSTRACT

The invention provides artificial chromosome constructs containing foreign nucleic acid sequences, such as viral nucleic acid sequences, and methods of using these artificial chromosome constructs for therapy and recombinant virus production.

8 Claims, 3 Drawing Sheets

HVS-BAC Mutagenesis

Fig. 3A

HVS-BAC Mutagenesis

PCR

Fig. 3B

Stability of BAC plasmid, p25 v cosmid 14, EcoRV digest

Fig. 4

SEQUENCE LISTING

<160> NUMBER OF SEQ ID NOS: 16

<210> SEQ ID NO 1
<211> LENGTH: 18
<212> TYPE: DNA
<213> ORGANISM: Escherichia coli

<400> SEQUENCE: 1
aggccggata gcttgtgc                     18

<210> SEQ ID NO 2
<211> LENGTH: 19
<212> TYPE: DNA
<213> ORGANISM: Escherichia coli

<400> SEQUENCE: 2
cggaacagag agcgtcaca                    19

<210> SEQ ID NO 3
<211> LENGTH: 28
<212> TYPE: DNA
<213> ORGANISM: Escherichia coli

<400> SEQUENCE: 3

-continued ggatgaggat cggtacccat gattgaac                                  28

<210> SEQ ID NO 4
<211> LENGTH: 28
<212> TYPE: DNA
<213> ORGANISM: Escherichia coli

<400> SEQUENCE: 4
atactcatac tcgagctctt ccttttc                                   28

<210> SEQ ID NO 5
<211> LENGTH: 20
<212> TYPE: DNA
<213> ORGANISM: Herpes Simplex Virus

<400> SEQUENCE: 5
ccgaatgctc ctacaacaag                                           20

<210> SEQ ID NO 6
<211> LENGTH: 20
<212> TYPE: DNA
<213> ORGANISM: Herpes Simplex Virus

<400> SEQUENCE: 6
gtcttccggg gcgagttctg                                           20

<210> SEQ ID NO 7
<211> LENGTH: 20
<212> TYPE: DNA
<213> ORGANISM: Herpes Simplex Virus

<400> SEQUENCE: 7
ggtgtagccg tgcccctcag                                           20

<210> SEQ ID NO 8
<211> LENGTH: 20
<212> TYPE: DNA
<213> ORGANISM: Herpes Simplex Virus

<400> SEQUENCE: 8
gcagatacgt cccgctcagg                                           20

<210> SEQ ID NO 9
<211> LENGTH: 21
<212> TYPE: DNA
<213> ORGANISM: Herpes Simplex Virus

<400> SEQUENCE: 9
atcaacttcg actggcccTT c                                         21

<210> SEQ ID NO 10
<211> LENGTH: 21
<212> TYPE: DNA
<213> ORGANISM: Herpes Simplex Virus

<400> SEQUENCE: 10
ccgtacatgt cgatgttcac c                                         21

<210> SEQ ID NO 11
<211> LENGTH: 20
<212> TYPE: DNA
<213> ORGANISM: Herpes Simplex Virus

<400> SEQUENCE: 11

-continued

```
accgcttcct cttcgctttc                                              20

<210> SEQ ID NO 12
<211> LENGTH: 20
<212> TYPE: DNA
<213> ORGANISM: Herpes Simplex Virus

<400> SEQUENCE: 12
cccgcagaag gttgttggtg                                              20

<210> SEQ ID NO 13
<211> LENGTH: 27
<212> TYPE: DNA
<213> ORGANISM: Herpes Simplex Virus

<400> SEQUENCE: 13
cctctcgggc acagctgtgc gattgtg                                      27

<210> SEQ ID NO 14
<211> LENGTH: 28
<212> TYPE: DNA
<213> ORGANISM: Herpes Simplex Virus

<400> SEQUENCE: 14
aagcgtgacc gcagctggaa cacggctg                                     28

<210> SEQ ID NO 15
<211> LENGTH: 25
<212> TYPE: DNA
<213> ORGANISM: Herpes Simplex Virus

<400> SEQUENCE: 15
cgtgtctgca agcttacggc cagtc                                        25

<210> SEQ ID NO 16
<211> LENGTH: 29
<212> TYPE: DNA
<213> ORGANISM: Herpes Simplex Virus

<400> SEQUENCE: 16
ccatgccgct gaagcttatg gagcgcagg                                    29
```

ARTIFICIAL CHROMOSOME CONSTRUCTS CONTAINING FOREIGN NUCLEIC ACID SEQUENCES

PRIORITY INFORMATION

This application is a continuation of, and claims priority from, U.S. patent application Ser. No. 09/031,006 (now U.S. Pat. No. 6,277,621), which was filed on Feb. 26, 1998.

BACKGROUND OF THE INVENTION

This invention relates to artificial chromosome constructs containing foreign nucleic acid sequences, such as viral nucleic acid sequences, and methods of using these constructs for therapy and for recombinant virus production.

Artificial chromosomes are large, DNA-based vectors that have been used extensively in the construction of DNA libraries for complex genome mapping and analysis. Artificial chromosomes have been derived from yeast (yeast artificial chromosomes: YACs), bacteria (bacterial artificial chromosomes: BACs, and P1-derived artificial chromosomes: PACs), and mammals (mammalian artificial chromosomes: MACs), such as humans (human artificial chromosomes: HACs). These vectors include elements derived from chromosomes that are responsible for replication and maintenance, and are capable of stably maintaining large genomic DNA fragments.

Herpes Simplex virus (HSV) is the prototypic human herpes virus. Despite the fact that HSV is a human pathogen, there has been a great deal of interest in using HSV as a therapeutic agent. The HSV genome has been sequenced, and many HSV mutants have been generated and used specifically in this context. Generation of HSV mutants has been carried out by using drug selection or by co-transfection of cells with plasmid DNA, usually modified by insertion of a marker gene, and intact viral DNA. Mutants are identified by screening for either drug resistance or recombination and expression of the marker gene, or by plaque hybridization. Another method that has been used to generate herpes virus mutants involves the use of cosmid sets that, taken together, contain complete herpes virus genomes. For example, cosmid sets that contain the entire genomes of Pseudorabies virus (PRV), Varicella-Zoster virus (VZV), Herpes Simplex virus (HSV), Cytomegalovirus (CMV), and Epstein-Barr virus (EBV) have been created. In constructing complete viral genomes from these cosmids, viral sequences are released from the cosmid backbones and transfected into cells. Viral plaques are produced via recombination between the overlapping fragments, which together represent the entire genome. Specific mutations are made in the viral genomes by manipulating the cosmid DNA.

SUMMARY OF THE INVENTION

The invention provides artificial chromosome constructs containing foreign nucleic acid sequences, such as viral nucleic acid sequences, and methods of using these artificial chromosome constructs for therapy (e.g., gene therapy) and recombinant virus production.

Accordingly, in one aspect, the invention features an artificial chromosome construct containing a nucleic acid sequence that directs formation of a recombinant virus (e.g., a lytic or a non-lytic virus) upon introduction into a cell. Optionally, the artificial chromosome construct, either in the artificial chromosome portion or in the nucleic acid sequence portion, further includes a heterologous nucleic acid sequence that, for example, encodes a therapeutic gene product, such as a growth factor, a hormone, an enzyme, a vaccine antigen, a cytotoxin, an immunomodulatory protein, an antisense RNA molecule, or a ribozyme. The artificial chromosome portion of the construct can be derived from a bacterial artificial chromosome, a P1-derived artificial chromosome, a yeast artificial chromosome, or a mammalian (e.g., human) artificial chromosome. The recombinant virus encoded by the nucleic acid sequence included in the artificial chromosome construct can be a herpes virus, such as a herpes simplex virus. Other viruses that can be encoded by the nucleic acid sequence are listed below.

In another aspect, the invention features a method of producing a recombinant virus in a cell, for example, a cell in a mammal, in which an artificial chromosome construct as described above is introduced into the cell. This method can further involve introducing into the cell an amplicon that is packaged into a recombinant virion upon introduction of the artificial chromosome construct into the cell.

The invention also provides a method of introducing a heterologous nucleic acid sequence into a cell, for example, a cell in a mammal, in which an artificial chromosome construct as described above is introduced into the cell.

Also included in the invention is a method of killing a cell, for example, a cell in a mammal (e.g., a cancer cell), in which an artificial chromosome construct as described above is introduced into the cell.

The invention also features a cell having an artificial chromosome construct stably integrated into its genome. In one example, the artificial chromosome construct includes a nucleic acid sequence that encodes an HSV genome in which an immediate early gene is mutated or deleted (see below). The invention also includes methods of making these cells.

The invention provides many advantages. For example, when bacterial artificial chromosome constructs are employed in the invention, the constructs can be easily and efficiently propagated in bacteria. This is particularly advantageous in the case of constructs including viral genes that would be cytopathic if the constructs were propagated in mammalian cells. This is also advantageous in the manufacturing of recombinant viruses, because large-scale, bacterial culture methods can be used, rather than methods employing mammalian cell culture. An additional advantage of the invention is that, in contrast to cosmid-based systems for virus production (see above), which rely on recombination of several molecules to reconstitute a complete viral genome, an entire viral genome can be contained in a single artificial chromosome construct, providing increased efficiency and genetic stability. As is discussed further below, this is particularly advantageous in the trans packaging of amplicons into recombinant viruses using the methods of the invention.

Other features and advantages of the invention will be apparent from the following detailed description, the drawings, and the claims.

BRIEF DESCRIPTION OF THE DRAWINGS

FIG. 1 is a schematic representation of the HindIII fragment of plasmid BAC-TK. Fragments AB and CD correspond to nucleotides 47860–47150 and 47057–45582, respectively, of the HSV-1 strain 17 genome (Genbank accession numbers X14112, O00317, O00374, and S40593). "H" represents HindIII restriction sites, and "cm" and "tk" represent chloramphenicol and thymidine kinase coding sequences, respectively.

FIG. 3A is a schematic representation of a method for carrying out HSV-BAC mutagenesis. Briefly, homologous recombination is carried out between HSV-BAC and a construct containing (i) sequences complementary to UL53 ("53seq"), (ii) a kanamycin gene ("kan"), and (iii) sequences complementary to UL55 ("55seq"), resulting in the UL54 gene, which is present in the HSV genome between the UL53 and UL55 genes, being replaced by the kanamycin gene.

DETAILED DESCRIPTION

The invention provides artificial chromosome constructs that contain foreign nucleic acid sequences, such as viral nucleic acid sequences. Optionally, the artificial chromosome constructs also contain heterologous nucleic acid sequences, i.e., nucleic acid sequences that are not naturally a component of the artificial chromosome or the viral nucleic acid sequences. The artificial chromosome constructs of the invention can be used in methods for producing recombinant viruses in cells in vivo, for example, in therapy methods (e.g., gene therapy methods), or in vitro, for example, in recombinant virus production methods or in amplicon packaging.

Artificial chromosomes into which foreign nucleic acid sequences can be inserted for use in the invention include, for example, bacterial artificial chromosomes (BACs, e.g., pBeloBAC11 or pBAC108L; see, e.g., Shizuya et al., Proc. Natl. Acad. Sci. USA 89(18):8794–8797, 1992; Wang et al., Biotechniques 23(6):992–994, 1997), P1-based artificial chromosomes (PACs), yeast artificial chromosomes (YACs; see, e.g., Burke, Genet. Anal. Tech. Appl. 7(5):94–99 , 1990), and mammalian artificial chromosomes (MACs; see, e.g., Vos, Nat. Biotechnol. 15(12): 1257–1259, 1997; Ascenzioni et al., Cancer Lett. 118(2): 135–142, 1997), such as human artificial chromosomes (HACs).

Viral nucleic acid sequences that can be inserted into artificial chromosomes to generate the artificial chromosome constructs of the invention can be derived from any of a number of well known viruses, such as viruses that include a circular replication intermediate. For example, members of DNA virus families, e.g., the Herpeseviridae (e.g., HSV-1, HSV-2, VZV, CMV, EBV, HHV6, or HHV7), Adenoviridae, Poxviridae, Papovaviridae (e.g., papillomaviruses and polyomaviruses), Parvoviridae, and Hepadnaviridae families, can be used. Members of RNA virus families, the genomes of which can be made into DNA by standard molecular techniques, can also be used. For example, members of the Coronaviridae, Picornaviridae, Retroviridae, Caliciviridae, Togaviridae (e.g., flaviviruses), and Astroviridae families, which are single, plus stranded viruses, can be used. Also, members of the Paramyxoviridae, Orthomyxoviridae, Filoviridae, Rhabdoviridae, Arenaviridae, and Bunyaviridae families, which are single, negative stranded viruses, can be used. Double stranded RNA viruses, such as those of the family Reoviridae, can also be used in the invention.

As is discussed above, viral nucleic acid sequences are included in the artificial chromosome constructs of the invention, so that recombinant viruses are produced from the constructs upon introduction into cells. In some applications of the invention, it is desirable that the recombinant virus produced in this manner results in killing of the cell. In this case, the virus produced from the artificial chromosome construct can be a virus that kills the cell in which it is produced by, for example, inducing lysis or apoptosis of the cell. This is desirable, for example, if the cell is a cancer cell, such as a cancer cell of a nervous-system type tumor, for example, an astrocytoma, oligodendroglioma, meningioma, neurofibroma, glioblastoma, ependymoma, Schwannoma, neurofibrosarcoma, or medulloblastoma cell. Other types of tumor cells that can be killed, pursuant to the present invention, include, for example, melanoma, pancreatic cancer, prostate carcinoma, breast cancer, lung cancer, colon cancer, gastric cancer, fibrosarcoma, squamous cell carcinoma, neurectodermal, thyroid tumor, pituitary tumor, lymphoma, hepatoma, mesothelioma, and epidermoid carcinoma cells.

Other therapeutic applications in which killing of a target cell is desirable include, for example, ablation of keratinocytes and epithelial cells responsible for warts, ablation of cells in hyperactive organs (e.g., thyroid), ablation of fat cells in obese patients, ablation of benign tumors (e.g., benign tumors of the thyroid or benign prostatic hypertrophy), ablation of growth hormone-producing adenohypophyseal cells to treat acromegaly, ablation of mammotropes to stop the production of prolactin, ablation of ACTH-producing cells to treat Cushing's disease, ablation of epinephrine-producing chromaffin cells of the adrenal medulla to treat pheochromocytoma, and ablation of insulin-producing beta islet cells to treat insulinoma.

This effect can be augmented if the artificial chromosome construct also contains a heterologous nucleic acid sequence encoding one or more of, for example, a cytotoxin, an immunomodulatory protein (i.e., a protein that either enhances or suppresses a host immune response to an antigen), or a tumor antigen. Examples of immunomodulatory proteins include, e.g., cytokines (e.g., interleukins, for example, any of interleukins 1–15, α-, β-, or γ-interferons, tumor necrosis factor, granulocyte macrophage colony stimulating factor (GM-CSF), macrophage colony stimulating factor (M-CSF), and granulocyte colony stimulating factor (G-CSF)), chemokines (e.g., neutrophil activating protein (NAP), macrophage chemoattractant and activating factor (MCAF), RANTES, and macrophage inflammatory peptides MIP-1a and MIP-1b), complement components and their receptors, immune system accessory molecules (e.g., B7.1 and B7.2), adhesion molecules (e.g., ICAM-1, 2, and 3), and adhesion receptor molecules. Examples of tumor antigens that can be produced using the present methods include, e.g., the E6 and E7 antigens of human papillomavirus, EBV-derived proteins (Van der Bruggen et al., Science 254:1643–1647, 1991), mucins (Livingston et al., Cur. Opin. Immun. 4(5):624–629, 1992), such as MUC1 (Burchell et al., Int. J. Cancer 44:691–696, 1989), melanoma tyrosinase, and MZ2-E (Van der Bruggen et al., supra). (Also see WO 94/16716 for a further description of modification of viral vectors to include genes encoding tumor antigens or cytokines.) The heterologous nucleic acid sequence can be inserted into either the artificial chromosome portion of the construct or into the viral portion of the construct in any of these examples.

In other applications of the methods of the invention, it is desirable that a recombinant virus, produced upon introduction of an artificial chromosome construct of the invention into a cell, does not kill the cell. These applications include, for example, use of artificial chromosome constructs that contain a heterologous gene encoding a therapeutic gene product, such as a growth factor, a hormone, a vaccine antigen, an antisense RNA molecule, or a ribozyme (see below). These applications also include using artificial chromosome constructs to immunize against a virus encoded by the nucleic acid sequence included in the construct. It may be desirable in these applications that the virus produced from the artificial chromosome construct is attenuated or mutated so that it does not replicate and/or so that it cannot kill the cell in which it is produced by, for example, inducing lysis or apoptosis of the cell. Numerous appropriate mutant viruses having these characteristics are known and can readily be adapted for use in the invention by those of ordinary skill in the art. For example, in the case of HSV, the vectors of Geller (U.S. Pat. No. 5,501,979; WO 90/09441; American Type Culture Collection (ATCC), Rockville, Md., ATCC Accession Number 40544), Breakfield (EP 453,242-A1), Speck (WO 96/04395), Preston et al. (WO 96/04394), DeLuca (U.S. Pat. No. 5,658,724), and Martuza (U.S. Pat. No. 5,585,096) can be adapted for use in such methods. Specific examples of attenuated HSV mutants that can be used include HF (ATCC VR-260), MacIntyre (ATCC VR-539), MP (ATCC VR-735); HSV-2 strains G (ATCC VR-724) and MS (ATCC VR-540); as well as mutants having mutations in one or more of the following genes: the immediate early genes ICP0, ICP4, ICP22, ICP27, and ICP47 (U.S. Pat. No. 5,658,724); genes necessary for viral replication, VL9, VL5, VL42, DNA pol, and ICP8; the γ34.5 gene; the ribonucleotide reductase gene; the VP16 gene (i.e., Vmw65, WO 91/02788; WO 96/04395; WO 96/04394); and the gH, gL, gD or gB genes (WO 92/05263, 94/21807, 94/03207).

An appropriate therapeutic product to be encoded by a heterologous nucleic acid sequence included in this type of artificial chromosome construct (i.e., a construct that results in production of a non-lytic virus upon introduction into a cell) can readily be selected by one skilled in the art, depending on the desired result. For example, the heterologous gene product can be a protein, such as a growth factor (e.g., brain-derived neurotrophic factor (BDNF), nerve growth factor (NGF), VGF, or VEGF), an enzyme, a hormone, or a vaccine antigen. Specific examples of protein gene products that can be produced in the invention include, e.g., tyrosine hydroxylase 1, 2, or 3, which can be used in the treatment of Parkinson's disease; Nerve Growth Factor (NGF, e.g., the NGF P subunit), which can be used in the treatment of Parkinson's disease; hypoxanthine-guanine phosphoribosyl transferase, which can be used in the treatment of Lesch-Nyhan disease; β-hexosaminidase α-chain, which can be used in the treatment of Tay-Sachs and Sandhoff's diseases; Human Immunodeficiency Virus (HIV) nef, which can be used in the treatment of the neurological symptoms of HIV, and insulin, which can be used in the treatment of diabetes. Other protein gene products that can be produced using the methods of the invention include, for example, signal transduction enzymes, e.g., Protein Kinase C; transcription factors, e.g., c-fos, NF-Kβ; oncogenes, e.g., erbB, erbB-2/neu, and ras; neurotransmitter receptors, e.g., glutamate receptor, dopamine receptor, and adenosine deaminase receptor (WO 92/10564, WO 89/12109, EP 0 420 911); and the cystic fibrosis protein (WO 91/02796, WO 92/05273, and WO 94/12649).

The therapeutic product can also be an RNA molecule, such as an antisense RNA molecule that, by hybridization interactions, can be used to block expression of a cellular or pathogen mRNA. Alternatively, the RNA molecule can be a ribozyme (e.g., a hammerhead or a hairpin-based ribozyme) designed either to repair a defective cellular RNA, or to destroy an undesired cellular or pathogen-encoded RNA (see, e.g., Sullenger, Chem. Biol. 2(5):249–253, 1995; Czubayko et al., Gene Ther. 4(9):943–949, 1997; Rossi, Ciba Found. Symp. 209:195–204, 1997; James et al., Blood 91(2):371–382, 1998; Sullenger, Cytokines Mol. Ther. 2(3):201–205, 1996; Hampel, Prog. Nucleic Acid Res. Mol. Bio. 58:1–39, 1998; Curcio et al., Pharmacol. Ther. 74(3):317–332, 1997).

The components of the artificial chromosome constructs of the invention can be assembled using standard methods. For example, as is described further below, a viral sequence can be inserted into an artificial chromosome by cotransfection of cells with (i) a construct containing the artificial chromosome, flanked by sequences homologous to regions of the viral genome, and (ii) the viral genome, so that recombination takes place in the cells, resulting in production of a recombinant virus including the artificial chromosome. Also as is described further below, recombinant DNA molecules can be isolated from cells in which an artificial chromosome construct and viral nucleic acid sequences have been co-transfected, leading to production of a recombinant virus by homologous recombination, and the isolated DNA molecule can be manipulated to insert or delete a gene, as desired. Direct cloning methods, employing unique sites in the viral genome and the artificial chromosome, can also be used to assemble the components of the artificial chromosome constructs of the invention.

The location within an artificial chromosome into which viral or heterologous nucleic acid sequences are inserted will vary depending, for example, on whether disruption of a particular viral function is desired. For example, if it is desired that the artificial chromosome construct includes viral sequences that will not lead to the production of replicable virus in cells (see above), then the artificial chromosome and the viral sequences can be combined so that a nucleic acid sequence that is essential for viral replication is disrupted. Similarly, insertion of a heterologous nucleic acid sequence can be used to disrupt an essential viral gene. Examples of essential genes in HSV, for example, are described above.

Alternatively, it may be desirable to have the artificial chromosome construct include viral sequences that will lead to the production of a replicable virus in cells (see above). In this case, recombination between the artificial chromosome and the viral nucleic acid sequence to generate an artificial chromosome construct (or introduction of a heterologous nucleic acid sequence) can be carried out in a non-essential region of the virus genome. For example, in the case of HSV, such an insertion can be in the thymidine kinase gene (UL23, see below; this insertion can be made alone or in combination with another insertion), in any one or more of the following genes: RL1, RL2 (i.e., IE110), the locus encoding latency associated transcripts, UL2 (the uracil-DNA glycosylase gene), UL3, UL4, UL10, UL11, UL13, UL16, UL20, UL24, UL40 (the small subunit of ribonucleotide reductase), UL41 (virion host shut-off factor), UL43, UL44, UL45, UL46, UL47, UL50, UL55, UL56, US1 (IE68), US2, US3 (the protein kinase gene), US4 (the glycoprotein G gene), US5, US7 (the glycoprotein I gene), US8 (the glycoprotein E gene), US9, US10, US11, and US12 (IE12), or in an intergenic sequence.

A heterologous nucleic acid sequence can be inserted into an artificial chromosome construct in a location that renders it under the control of a regulatory sequence of the artificial chromosome or viral nucleic acid sequences. Alternatively, the heterologous nucleic acid sequence can be inserted as part of an expression cassette that includes regulatory elements, such as promoters or enhancers. Appropriate regulatory elements can be selected by one of ordinary skill in the art based on, for example, the desired tissue-specificity and level of expression. For example, a cell-type specific or tumor-specific promoter can be used to limit expression of a gene product to a specific cell type. This is particularly useful, for example, when a cytotoxic, immunomodulatory, or tumor antigenic gene product is being produced in a tumor cell in order to facilitate its destruction. In addition to using tissue-specific promoters, local administration of an artificial chromosome construct can result in localized expression.

Examples of non-tissue specific promoters that can be used in the invention include the early Cytomegalovirus (CMV) promoter (U.S. Pat. No. 4,168,062) and the Rous Sarcoma Virus promoter (Norton et al., Molec. Cell Biol. 5:281, 1985). Also, HSV promoters, such as HSV-1 IE and IE 4/5 promoters, can be used.

Examples of tissue-specific promoters that can be used in the invention include, for example, the desmin promoter, which is specific for muscle cells (Li et al., Gene 78:243, 1989; Li et al., J. Biol. Chem. 266:6562, 1991; Li et al., J. Biol. Chem. 268:10403, 1993); the enolase promoter, which is specific for neurons (Forss-Petter et al., J. Neuroscience Res. 16(1):141–156, 1986); the β-globin promoter, which is specific for erythroid cells (Townes et al., EMBO J. 4:1715, 1985); the tau-globin promoter, which is also specific for erythroid cells (Brinster et al., Nature 283:499, 1980); the growth hormone promoter, which is specific for pituitary cells (Behringer et al., Genes Dev. 2:453, 1988); the insulin promoter, which is specific for pancreatic beta cells (Selden et al., Nature 321:545, 1986); the glial fibrillary acidic protein promoter, which is specific for astrocytes (Brenner et al., J. Neurosci. 14:1030, 1994); the tyrosine hydroxylase promoter, which is specific for catecholaminergic neurons (Kim et al., J. Biol. Chem. 268:15689, 1993); the amyloid precursor protein promoter, which is specific for neurons (Salbaum et al., EMBO J. 7:2807, 1988); the dopamine β-hydroxylase promoter, which is specific for noradrenergic and adrenergic neurons (Hoyle et al., J. Neurosci. 14:2455, 1994); the tryptophan hydroxylase promoter, which is specific for serotonin/pineal gland cells (Boularand et al., J. Biol. Chem. 270:3757, 1995); the choline acetyltransferase promoter, which is specific for cholinergic neurons (Hersh et al., J. Neurochem. 61:306, 1993); the aromatic L-amino acid decarboxylase (AADC) promoter, which is specific for catecholaminergic/5-HT/D-type cells (Thai et al., Mol. Brain Res. 17:227, 1993); the proenkephalin promoter, which is specific for neuronal/spermatogenic epididymal cells (Borsook et al., Mol. Endocrinol. 6:1502, 1992); the reg (pancreatic stone protein) promoter, which is specific for colon and rectal tumors, and pancreas and kidney cells (Watanabe et al., J. Biol. Chem. 265:7432, 1990); and the parathyroid hormone.=related peptide (PTHrP) promoter, which is specific for liver and cecum tumors, and neurilemoma, kidney, pancreas, and adrenal cells (Campos et al., Mol. Rnfovtinol. 6:1642, 1992).

Examples of promoters that function specifically in tumor cells include the stromelysin 3 promoter, which is specific for breast cancer cells (Basset et al., Nature 348:699, 1990); the surfactant protein A promoter, which is specific for non-small cell lung cancer cells (Smith et al., Hum. Gene Ther. 5:29–35, 1994); the secretory leukoprotease inhibitor (SLPI) promoter, which is specific for SLPI-expressing carcinomas (Garver et al., Gene Ther. 1:46–50, 1994); the tyrosinase promoter, which is specific for melanoma cells (Vile et al., Gene Therapy 1:307, 1994; WO 94/16557; WO 93/GB1730); the stress inducible grp78/BiP promoter, which is specific for fibrosarcoma/tumorigenic cells (Gazit et al., Cancer Res. 55(8):1660, 1995); the AP2 adipose enhancer, which is specific for adipocytes (Graves, J. Cell. Biochem. 49:219, 1992); the α-1 antitrypsin transthyretin promoter, which is specific for hepatocytes (Grayson et al., Science 239:786, 1988); the interleukin-10 promoter, which is specific for glioblastoma multiform cells (Nitta et al., Brain Res. 649:122, 1994); the c-erbB-2 promoter, which is specific for pancreatic, breast, gastric, ovarian, and non-small cell lung cells (Harris et al., Gene Ther. 1:170, 1994); the α-B-crystallin/heat shock protein 27 promoter, which is specific for brain tumor cells (Aoyama et al., Int. J. Cancer 55:760, 1993); the basic fibroblast growth factor promoter, which is specific for glioma and meningioma cells (Shibata et al., Growth Fact. 4:277, 1991); the Epidermal Growth Factor Receptor promoter, which is specific for squamous cell carcinoma, glioma, and breast tumor cells (Ishii et al., Proc. Natl. Acad. Sci. USA 90:282, 1993); the mucin-like glycoprotein (DF3, MUC1) promoter, which is specific for breast carcinoma cells (Abe et al., Proc. Natl. Acad. Sci. USA 90:282, 1993); the mts1 promoter, which is specific for metastatic tumors (Tulchinsky et al., Proc. Natl. Acad. Sci. USA 89:9146, 1992); the NSE promoter, which is specific for small-cell lung cancer cells (Forss-Petter et al., Neuron 5:187, 1990); the somatostatin receptor promoter, which is specific for small cell lung cancer cells (Bombardieri et al., Eur. J. Cancer 31 A:184, 1995; Koh et al., Int. J. Cancer 60:843, 1995); the c-erbB-3 and c-erbB-2 promoters, which are specific for breast cancer cells (Quin et al., Histopathology 25:247, 1994); the c-erbB4 promoter, which is specific for breast and gastric cancer cells (Rajkumar et al., Breast Cancer Res. Trends 29:3, 1994); the thyroglobulin promoter, which is specific for thyroid carcinoma cells (Mariotti et al., J. Clin. Endocrinol. Meth. 80:468, 1995); the α-fetoprotein promoter, which is specific for hepatoma cells (Zuibel et al., J. Cell. Phys. 162:36, 1995); the villin promoter, which is specific for gastric cancer cells (Osborn et al., Virchows Arch. A. Pathol. Anat. Histopathol. 413:303, 1988); and the albumin promoter, which is specific for hepatoma cells (Huber, Proc. Natl. Acad. Sci. USA 88:8099, 1991).

As noted above, the artificial chromosome constructs of the invention can be used in in vivo methods, for example, to introduce a therapeutic gene product into a cell, or to kill a cell, either directly or indirectly, through a lytic viral intermediate. To carry out these methods, the artificial chromosome constructs can be administered by any conventional route used in medicine. As general guidance, an artificial chromosome construct of the invention can be administered directly into the tissue in which an effect, e.g., expression, is desired, for example, by direct injection or by surgical methods (e.g., stereotactic injection into a brain tumor; Pellegrino et al., Methods in Psychobiology (Academic Press, New York, N.Y., 67–90, 1971)). An additional method that can be used to administer artificial chromosome constructs into the brain is the convection method described by Bobo et al. (Proc. Natl. Acad. Sci. USA 91:2076–2080, 1994) and Morrison et al. (Am. J. Physiol. 266:292–305, 1994). In the case of tumor treatment, as an alternative to direct tumor injection, surgery can be carried out to remove the tumor, and the artificial chromosome constructs of the invention inoculated into the resected tumor bed to ensure destruction of any remaining tumor cells.

Alternatively, the construct can be administered via a parenteral route, e.g., by an intravenous, subcutaneous, intraperitoneal, intradermal, intraepidermal, or intramuscular route, or via a mucosal surface, e.g., an ocular, intranasal, pulmonary, oral, intestinal, rectal, vaginal, or urinary tract surface. An artificial chromosome construct formulated in association with bupivacaine (see below) is advantageously administered into muscle tissue. When a neutral or anionic liposome or a cationic lipid, such as DOTMA or DC-Chol (see below), is used, the formulation can be advantageously injected via intravenous, intranasal (aerosolization), intramuscular, intradermnal, or subcutaneous routes. An artificial chromosome construct in a naked form can advantageously be administered via intramuscular, intradermal, or subcutaneous routes.

Any of a number of well known formulations for introducing nucleic acid molecules into cells in mammals can be used in the invention. (See, e.g., *Remington's Pharmaceutical Sciences* (18$^{th}$ edition), ed. A. Gennaro, 1990, Mack Publishing Co., Easton, Pa.) For example, the artificial chromosome constructs can be used in a naked form, free of any packaging or delivery vehicle. The artificial chromosome constructs can be simply diluted in a physiologically acceptable solution, such as sterile saline or sterile buffered saline, with or without a carrier. Artificial chromosome constructs can also be administered in calcium phosphate solutions.

The artificial chromosome constructs can be also associated with agents that facilitate cellular uptake of nucleic acid molecules. For example, the artificial chromosome constructs can be complemented with a chemical agent that modifies cellular permeability, such as bupivacaine (see, e.g., WO 94/16737), encapsulated into a liposome, or associated with cationic lipids or silica, gold, or tungsten microparticles.

Anionic and neutral liposomes are well known in the art (see, e.g., *Liposomes: A Practical Approach*, RPC New Ed, IRL press (1990), for a detailed description of methods for making liposomes) and are useful for delivering a large range of products, including nucleic acid molecules. Cationic lipids are also well known and are commonly used for gene delivery. Such lipids include Lipofectin™, also known as DOTMA (N-[1-(2,3-dioleyloxy)propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives, such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid, such as DOPE (dioleyl phosphatidylethanolamine), as, for example, described in WO 90/11092.

Other transfection-facilitating compounds can be added to formulations containing cationic liposomes. A number of these compounds are described in, e.g., WO 93/18759, WO 93/19768, WO 94/25608, and WO 95/2397. They include, e.g., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (Nature 356:152, 1992). In this case, the microparticle-coated nucleic acid molecules can be injected via intradermal or intraepidermal routes using needleless injection devices ("gene gun"), such as those described in U.S. Pat. No. 4,945,050, U.S. Pat. No. 5,015,580, and WO 94/24263.

The amount of artificial chromosome construct to be administered depends, e.g., on the specific goal to be achieved, the strength of any promoter used in the construct, the condition of the mammal intended for administration (e.g., the weight, age, and general health of the mammal), the mode of administration, and the type of formulation. In general, a therapeutically or prophylactically effective dose of, e.g., from about 1 ng to about 1 mg, preferably, from about 10 μg to about 800 μg, is administered to human adults. The administration can be achieved in a single dose or repeated at intervals.

In addition to being used in therapeutic methods, the artificial chromosome constructs of the invention can be used to cheaply and efficiently produce recombinant viruses in vitro. As is discussed above, prior viral production methods have employed cosmid sets containing portions of viral genomes that are recombined to generate complete viral genomes upon introduction into cells. This method can result in instability of the viral genome. The artificial chromosome constructs of the invention by-pass the need for recombination between multiple cosmids, leading to enhanced stability of the produced viral genome. In addition, the artificial chromosome constructs of the invention, such as those including BACs, can be propagated in host systems, such as bacteria, that are not adversely affected by the presence of viral genes that are harmful to mammalian cells. Standard methods can be used for introducing mutations into such constructs or for introducing heterologous genes to be included in a recombinant viral vector.

The artificial chromosome constructs of the invention also enable efficient packaging of amplicons into recombinant viral particles (see, e.g., WO 97/05263). Amplicons are plasmids containing a gene (e.g., any of the heterologous nucleic acid sequences described above) under the control of regulatory sequences (e.g., any of the promoters or enhancers described above and, optionally, sequences that direct processing of mRNA, such as a polyadenylation sequence), a viral origin of replication, and viral packaging signals. As is described further below in reference to HSV, when an amplicon is co-transfected into a cell with an artificial chromosome construct of the invention, which includes viral DNA that results in recombinant virus formation upon introduction into a cell, the amplicon is packaged in a virion, thus providing an effective gene delivery vector. Recombinant viruses produced using these methods can be used, for example, as viral vectors for therapy, e.g., gene therapy.

The artificial chromosome constructs of the invention can also be used in methods for generating cell lines that can be used, for example, for virus production. As a specific example, an HSV-BAC construct can be made in which any one or any combination of the immediate early genes (i.e., ICP0, ICP4, ICP22, ICP27, and ICP47) is mutated or deleted, using standard methods, such as those described above. Optionally, a gene encoding a selectable marker, such as an antibiotic resistance gene (e.g., a neomycin resistance gene), can be inserted into the viral genome in a non-essential region (see above) or into the BAC. This construct can then be transfected into cells (e.g., Vero cells, see above) using standard methods, and clones containing integrated HSV can be selected by culturing the cells in the presence of, for example, the antibiotic. Cells produced in this manner do not, without further manipulation, produce virus, due to the missing immediate early gene(s). Thus, the cells can be cultured in the absence of the cytotoxicity that can be associated with viral production. When it is desired to induce virus production in these cells, the missing immediate early gene(s) can be introduced into the cells by transfection.

These methods provide significant advantages over prior methods which, in requiring the simultaneous introduction of multiple, large plasmids into a single cell, are inefficient and expensive. In addition, it is straightforward to carry out deletion or mutation of genes propagated in bacteria, as is possible when using the bacterial artificial chromosome constructs of the invention. In contrast, attempting to accomplish this using cell lines is extremely difficult, if not impossible. Finally, although described above in reference to HSV-BAC, these methods can be readily adapted to employ the use of any of the artificial chromosome constructs described above.

Experimental Results
Generation of Recombinant Viruses and BAC Plasnmids

Figure 1:
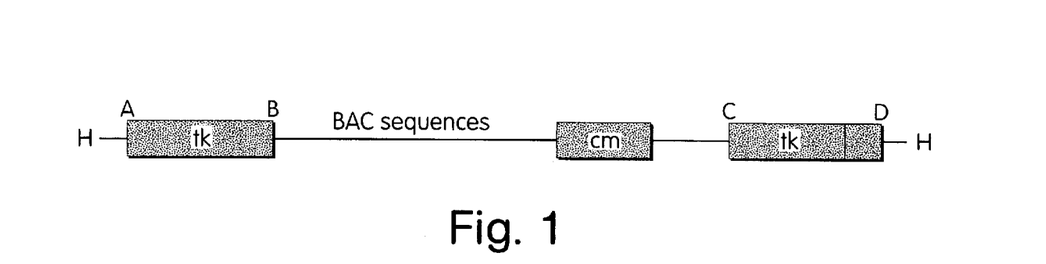

We used bacterial artificial chromosome (BAC) technology to clone the entire HSV genome. A plasmid, BAC-TK, was constructed with viral tk sequences flanking the signals necessary for chromosomal maintenance in bacteria and the chloramphenicol resistance gene (FIG. 1). This plasmid was linearized and co-transfected with HSV-1 infectious DNA into Vero cells (ATCC CRL 1587). The resultant virus stocks were screened with 100 $\mu$M acyclovir (ACV), and resistant viruses were isolated and plaque purified. Southern blot and PCR analysis confirmed insertion of BAC and chloramphenicol sequences within the tk locus. The recombinant virus was designated HSV-BAC-TK.

Vero cells were infected for 2 hours with HSV-BAC-TK at an m.o.i. of 3, harvested, and DNA was extracted as is described below in Materials and Methods. Isolated circular DNA was electroporated into $E.$ $coli$ and recombinant colonies were screened for resistance to chloramphenicol. Bacteria that were resistant to the antibiotic were subjected to further analysis. Briefly, DNA was extracted from 11 colonies and subjected to PCR analysis using primer sets corresponding to HSV genes US6, UL10, UL30, and UL40. All 11 clones tested were positive for all four primer sets. DNA was extracted from 8 of the 11 clones and digested with EcoRI, EcoRV, and HindIII. The results showed that the entire genome of HSV had been cloned.

Rescue of Infectious Virus Progeny From HSV-BAC Clones

Figure 2:
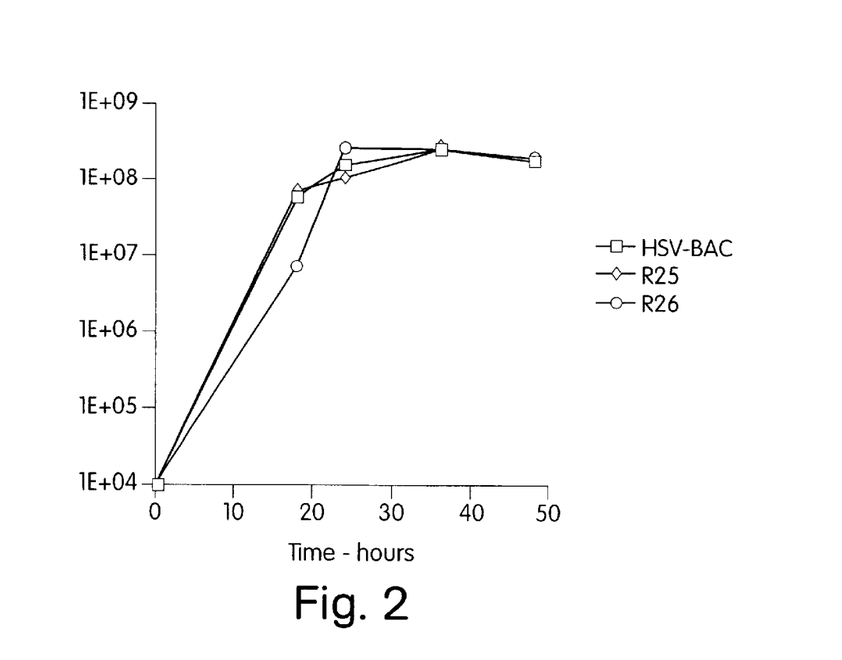
FIG. 2 is a graph showing one-step growth curves for HSV-BAC, r25, and r26 (see Experimental Results, below).

Two clones from the original 8, p25 and p26, were selected for further analysis. Transfection of these BAC plasmids resulted in plaques formation after two days. Rescued virus was amplified, and the viral DNA was extracted and digested with restriction endonucleases. The restriction endonuclease patterns of rescued viruses r25 and r26 were identical to those of p25, p26, and HSV-BAC-TK. To determine whether the rescued viruses behaved similarly to the parental virus, all three viruses were tested in a one step growth curve (FIG. 2). The results show that there is little or no difference in the growth rates of the parental input virus and the bacterially rescued viruses over time.

Construction and Characterization of an HSV UL54 Mutant

Figure 3A:
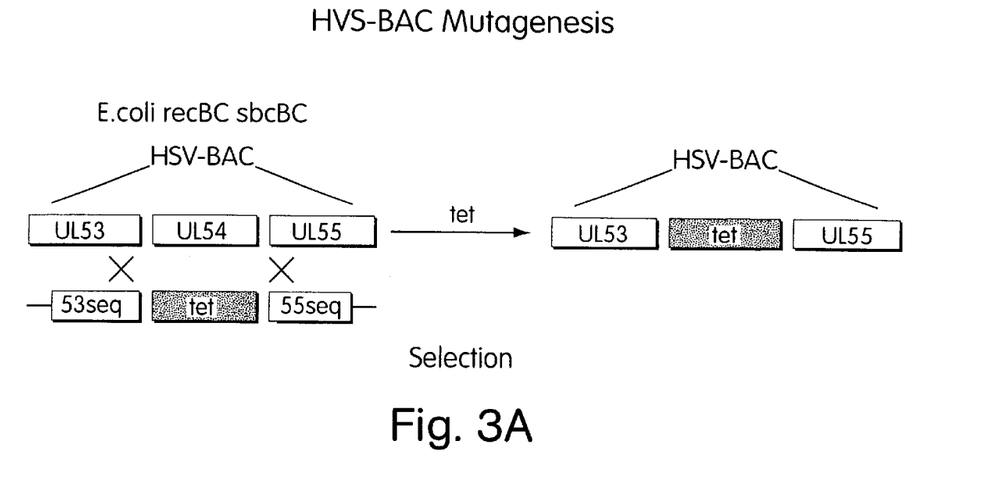
Figure 3B:
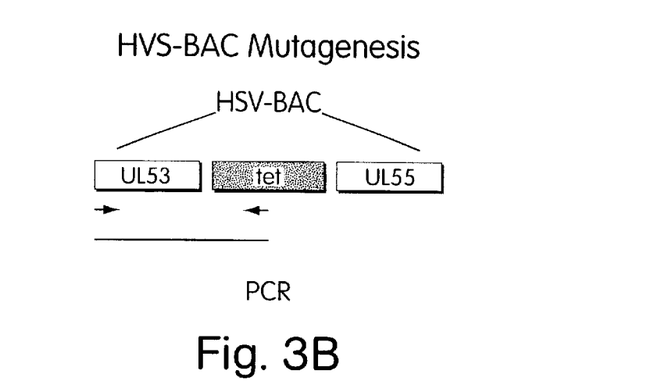
FIG. 3B is a schematic representation of PCR analysis that can be used to characterize clones in which the homologous recombination event described above in reference to FIG. 3A has taken place.

To illustrate the power of bacterial genetics in the construction of HSV mutants, the essential HSV gene, UL54, can be deleted as follows. (See FIGS. 3A and 3B.) The gene product of the UL54 gene, ICP27, plays many roles in HSV infection. The protein, which is essential for viral growth, is found predominantly in the nucleus, where it inhibits pre-mRNA splicing, interacts with the host cell's small nuclear ribonucleoprotein particles, binds to RNA, prevents the nucleocytoplasmic transport of intron-containing mRNAs, and regulates late-gene protein synthesis by facilitating the export of late viral RNAs.

To clone the flanking sequences for homologous recombination, two primer sets can be used. One set binds to a sequence that lies immediately upstream of the UL54 coding sequence and to a sequence about 1 kb upstream from this site, i.e., in the UL53 gene. The second set binds to sequences immediately 3' of the UL54 stop codon and to a sequence about 1 kb downstream from this site, i.e., in the UL55 gene. PCR fragments generated using these primers can be cloned into placi, generating p53-laci-55. Kanamycin coding sequences can be amplified by PCR and cloned in frame with the α-complementation lacZ sequences of p53-placi-55 to create p53-laci-kan-UL55. Homologous recombination between this plasmid and BAC DNA results in replacement of the HSV UL54 coding sequences with the laci promoter driving the α-complementation lacZ/kanamycin fusion sequences. p53-placi-kan-55 sequences can be released from the plasmid backbone, gel purified, and transformed into competent $E.$ $coli$ that contain p25. Recombinants can then be screened for their ability to grow on kanamycin, IPTG, and chloramphenicol plates. Southern hybridization can be used to confirm the presence of the mutation.

A clone having the correct mutation, which could be designated pΔUL54, could be further analyzed, as follows. The growth kinetics of rΔUL54, the rescued virus from pΔUL54, r25, HSV-BAC-TK, and wild type HSV strain F could be compared in 2-2 and Vero cells. 2-2 cells are a stable cell line that constitutively express ICP27, and thus are able to complement the UL54 defect. All four viruses would be expected to replicate to wild type levels in 2-2 cells, but rΔUL54 would not be expected to grow on Vero cells. Restriction endonuclease patterns of DNA extracted from the rescued mutant viruses or from input plasmid DNA could be carried out to confirm that BAC plasmids remain stable during the mutagenesis procedure.

HSV-BAC DNA Packages Amplicons

Vectors based on HSV have been used extensively for gene transfer. HSV-plasmid vectors (amplicons) contain a eukaryotic expression cassette and the HSV signals for replication and packaging. The amplicon vector is replicated and packaged into virions when co-propagated with a helper virus, either wild type virus, replication-defective virus, or virus generated from HSV cosmids. In fact, a modified cosmid set has been used to produce amplicon preparations that are free of contaminating helper virus (Fraefel et al., supra). However, herpes virus cosmids are prone to deletion and rearrangement and, further, are often heterogeneous in nature. A BAC clone of HSV overcomes these problems.

Figure 4:
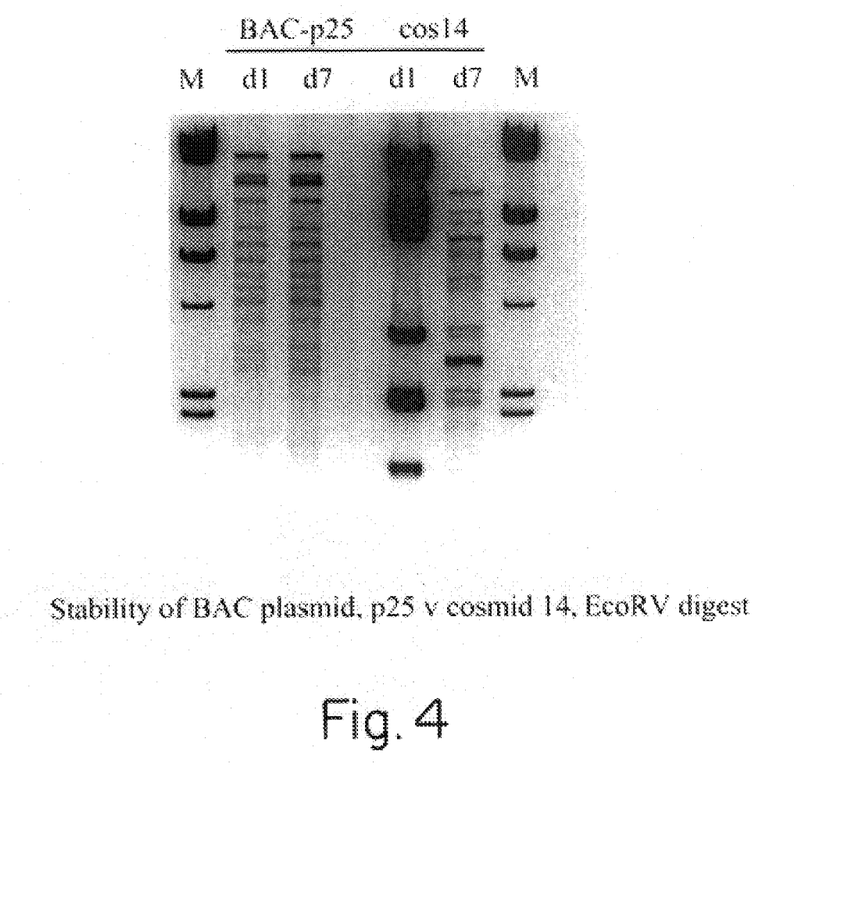
FIG. 4 is a photograph of a gel showing the results of an experiment in which the stability of the BAC plasmid p25 was compared to the stability of cosmid 14 (Cunningham et al., Virology 197(1): 116–124, 1993).

To assess the stability of HSV-BAC clones, as compared to HSV cosmid clones, we purified and digested DNA isolated from bacterial cultures grown continuously for either 1, 3, or 7 days. (See FIG. 4 for the results obtained on samples taken at days 1 and 7.) The restriction endonuclease pattern of p25 remained unchanged throughout this period, while the restriction endonuclease pattern of cosmid 14 (Cunningham et al., supra) was altered drastically. Heterogeneity in the bacterial population was appraised by streaking out $E.$ $coli$ containing either p25 or cosmid 48 (Cunningham et al., supra) and mini-prepping 5 clones each. The results showed that $E.$ $coli$ containing BAC clones are homogeneous, while $E.$ $coli$ containing cosmid clones are heterogeneous in nature. Thus, maintenance of HSV sequences in BACs is preferable for the production of homogenous, infectious viral DNA for therapeutic purposes.

Trans functions were tested by determining the ability of HSV-BAC DNA to package amplicon plasmid DNA. An amplicon plasmid containing the Green Fluorescent Protein (GFP) gene under the control of the IE 4/5 promoter, or an amplicon plasmid containing a lacZ gene under the control of the Rous Sarcoma Virus (RSV) promoter (pHSVLac), was co-propagated with either transfected p25, HSV cosmid DNA (6, 28, 14, 56, and 48; Cunningham et al., supra), or infectious F strain viral DNA (ATCC VR-733). Cells were harvested after four days and infectious particles were titered by infecting fresh monolayers and counting either plaques, green cells, or blue cells (Table 2). The results showed that HSV-BAC DNA could package amplicons more efficiently than cosmid DNA and infectious viral DNA. These data show that HSV-BAC, with appropriate modifications, can be used as a powerful vector for gene transfer.

Materials and Methods

Viruses and Cells

Vero and Vero 2-2 cells were propagated and assayed for drug susceptibility as described by Coen et al. (Virology 168:221–231, 1989). Virus titers were determined in triplicate on Vero cells. Recombinant viruses were plaque-purified two times and the mutations were confirmed by Southern blot hybridization and PCR analysis.

Plasmids

Plasmid pTK-AB was created by subcloning the BglI-IEcoRI fragment from pXholf (the XhoI F fragment of HSV-1 strain 17 cloned into plasmid pAT153) into the BamHI/EcoRI sites of pHSVlac (Geller etal., supra). The tk-containing plasmid, BH13 (Horsburgh et al., Cell 86(6):949–959, 1996) was digested with PstI and XhoI, to release the 3' end of the tk gene, and the fragment was subcloned into the PstI MXhoI site of pSC1180, creating plasmid TK-CD. Plasmids TK-AB and TK-CD were digested with HindIII/MscI and HindIII/SalI, respectively, and the resulting fragments were subcloned into the HpaI/SalI sites of pBeloBAC (Dr. H. Shizuya and Dr. M. Simon, Department of Biology, California Institute of Technology, Pasadena, Calif.) to create plasmid pBAC-TK (FIG. 1).

pLaci was generated by digesting pBluescript KS (Stratagene) with SacI and NaeI, blunt ending with T4 DNA polymerase, and religating. UL53, UL55, and kanamycin sequences were amplified by PCR using primers containing PvuII, HindIII, and KpnI/XhoI sites, respectively (Table 1). The UL53 fragment was digested with PvuII and cloned into the unique PvuII site of pLaci, creating UL53-pLaci. The orientation of the fragment was confirmed by restriction enzyme digestion. Likewise, the UL55 fragment was digested with HindIII and cloned into the HindIII site of UL53-pLaci, creating UL53-pLaci-UL55. The orientation was confirmed by restriction digestion. The kanamycin fragment was digested with KpnI and XhoI, and cloned into KpnI/XhoI-digested UL53-pLaci-UL54. This results in an in-frame fusion of lacZ α-complementation and kanamycin sequences. This plasmid was called UL53-pLaci-kan-UL55. pHSV-GFP (Green Fluorescent Protein) was constructed by replacing lacZ sequences in pHSVLac (Geller, supra) with GFP sequences.

Polymerase Chain Reaction (PCR)

PCR-amplified fragments were obtained using viral genomic DNA or plasmid DNA as template and the oligonucleotides listed in Table 1 as primers. Taq DNA polymerase (Promega) was used to amplify the region of interest, according to the recommendations of Sambrook et al. (Molecular Cloning, A Laboratory Manual, Cold Spring Harbor Laboratory Press, Cold Spring Harbor, N.Y., 1989) and 30 cycles (95° C., 1 minute, 55° C., 1 minute, 72° C, 1 minute) were carried out in a Perkin Elmer GeneAmp 2400.

Virus Construction

Plasmid BAC-TK was digested with HindIII and co-transfected into Vero cells with infectious HSV-1 F strain DNA, as described by Chiou et al. (Virology 145(2):213–226, 1985). DNA from plaques that were resistant to 100 $\mu$M acyclovir (ACV) was screened by PCR using primers that correspond to chloramphenicol sequences (Table 1). From each of two independent transfections, one recombinant virus was plaque-purified two times and the mutation confirmed by Southern blot hybridization. This virus was designated HSV-BAC.

Isolation of HSV-BAC DNA and BAC Plasmids

One hundred mm dishes of confluent Vero cells were infected with HSV-BAC at an m.o.i. of 3. Infections were allowed to proceed for two hours, the supernatants were removed, and 1 ml of DNAzole (Gibco) was added. DNA, obtained from the cell lysate following the manufacturer's protocol, was resuspended in 100 $\mu$l of TE. One $\mu$l of DNA was added to an equal volume of water and electroporated into 25 $\mu$l of electro-competent E. coli, strain DH10B (Hanahan et al., Methods Enzymol. 204:63–113, 1991) using a cell-porator (Gibco) and conditions recommended by the manufacturer. The bacteria were allowed to recover by incubation at 37° C. in LB broth, plated out onto LB agar plates containing chloramphenicol (12.5 ng/ml), and incubated at 37° C. overnight. BAC plasmids were isolated from E. coli using an alkaline-lysis procedure and screened by PCR. Four sets of primers were used to amplify sequences in US6, UL10, UL30, and UL40 (Table 1). Two $\mu$g of DNA from clones that were positive for all primers sets was transfected into a 100 mm dish of Vero cells using 18 $\mu$l of lipofectamine, and incubated at 34° C. Viral plaques were observed two days post-transfection.

BAC Mutagenesis p25-containing bacteria were made competent by $CaCl_2$ treatment. pUL53-pLaci-kan-UL55 was digested with XbaI, MluI, and ScaI, and the UL53-pLaci-kan-UL55 sequences were gel purified and transformed into competent p25 E. coli. The bacteria were allowed to recover for 2 hours at 37° C. in the presence of 1 mM IPTG, then plated out on kanamycin/IPTG plates (5 mg/ml and 1 mM, respectively). Mutations were confirmed by PCR and Southern blot hybridization. Mutant viruses were tested for growth on 2-2 and Vero cells.

Amplicon Production 2-2 cells were transfected with 1, 2, or 4 $\mu$g of either p25, HSV cosmid set 6, 28, 14, 56, and 48 (Cunningham et al., supra), or infectious HSV F strain DNA and 1 g of pHSV-GFP, as described by Fraefel et al. (J. Virol. 70(10):7190–7197, 1996). Cells were harvested after four days, frozen and thawed three times, the cellular debris was removed by centrifugation, and the supernatant was used to infect fresh monolayers. Titers were calculated by counting viral plaques and transduced green cells.

TABLE 1

Primers

| | |
|---|---|
| Chloramphenicol | 5'-AGGCCGGATAGCTTGTGC-3' (SEQ ID NO:1) |
| | 5'-CGGAACAGAGAGCGTCACA-3' (SEQ ID NO:2) |
| Kanamycin | 5'-GGATGAGGATCGGTACCCATGATTGAAC-3' (SEQ ID NO:3) |
| | 5'-ATACTCATACTCGAGCTCTTCCTITTTC-3' (SEQ ID NO:4) |
| US6 | 5'-CCGAATGCTCCTACAACAAG-3' (SEQ ID NO:5) |
| | 5'-GTCTTCCGGGGCGAGTTCTG-3' (SEQ ID NO:6) |
| UL10 | 5'-GGTGTAGCCGTGCCCCTCAG-3' (SEQ ID NO:7) |
| | 5'-GCAGATACGTCCCGCTCAGG-3' (SEQ ID NO:8) |
| UL30 | 5'-ATCAACTTCGACTGGCCCTTC-3' (SEQ ID NO:9) |
| | 5'-CCGTACATGTCGATGTTCACC-3' (SEQ ID NO:10) |
| UL40 | 5'-ACCGCTTCCTCTTCGCTFFC-3' (SEQ ID NO:11) |
| | 5'-CCCGCAGAAGGTTGTTGGTG-3' (SEQ ID NO:12) |
| UL53 | 5'-CCTCTCGGGCACAGCTGTGCGATTGTG-3' (SEQ ID NO:13) |
| | 5'-AAGCGTGACCGCAGCTGGAACACGGCTG-3' (SEQ ID NO:14) |
| UL55 | 5'-CGTGTCTGCAAGCTTACGGCCAGTC-3' (SEQ ID NO:15) |
| | 5'-CCATGCCGCTGAAGCTTATGGAGCGCAGG-3' (SEQ ID NO:16) |

TABLE 2

| | HSV-DNA + pAmplicon | | HSV-DNA + pUC |
|---|---|---|---|
| | t.u./ml | p.f.u./ml | p.f.u./ml |
| p25 | $3 \times 10^6$ | $9 \times 10^5$ | $1 \times 10^7$ |
| iDNA | $1.5 \times 10^5$ | n/d | n/d |
| Δa cosmids | $2 \times 10^5$ | n/a | n/a |
| wt cosmids | $3.5 \times 10^5$ | n/d | n/d |

Assays, as described in Materials and Methods, were repeated between 3 and 16 times to obtain averaged values.

n/a, not applicable; n/d, not done; t.u., transducing units; p.f.u., plaque-forming units. p25 BAC DNA, see text for details; iDNA, infectious F strain HSV DNA; Δa cosmids, HSV strain 17 cosmid set lacking "a" sites as described in Fraefel et al. (supra); wt cosmids, HSV strain 17 cosmid set as described in Cunningham et al. (supra).

All references cited herein are incorporated by reference in their entirety. Other embodiments are within the following claims.

What is claimed is:

1. A method of producing a recombinant virus in a cell, said method comprising introducing into said cell an artificial chromosome construct comprising a nucleic acid sequence that directs formation of a recombinant virus upon introduction into said cell.

2. The method of claim 1, wherein said cell is in a mammal.

3. The method of claim 1, further comprising introducing into said cell an amplicon that is packaged into a recombinant virion upon introduction of said artificial chromosome construct into said cell.

4. A method of introducing a heterologous nucleic acid sequence into a cell, said method comprising introducing into said cell an artificial chromosome construct comprising a nucleic acid sequence that directs formation of a recombinant virus upon introduction into said cell, wherein said artificial chromosome construct further comprises said heterologous nucleic acid sequence.

5. The method of claim 4, wherein said cell is in a mammal.

6. A method of killing a cell, said method comprising introducing into said cell an artificial chromosome construct comprising a nucleic acid sequence that directs formation of a lytic recombinant virus upon introduction into said cell.

7. The method of claim 6, wherein said cell is in a mammal.

8. The method of claim 6, wherein said cell is a cancer cell.

* * * * *